United States Patent
Onishi et al.

(10) Patent No.: US 8,051,714 B2
(45) Date of Patent: Nov. 8, 2011

(54) SENSING INSTRUMENT

(75) Inventors: Naoki Onishi, Sayama (JP); Hiroyuki Kukita, Sayama (JP); Shunichi Wakamatsu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 407 days.

(21) Appl. No.: 12/311,262

(22) PCT Filed: Sep. 27, 2007

(86) PCT No.: PCT/JP2007/069410
§ 371 (c)(1),
(2), (4) Date: May 7, 2009

(87) PCT Pub. No.: WO2008/041733
PCT Pub. Date: Apr. 10, 2008

(65) Prior Publication Data
US 2009/0308142 A1  Dec. 17, 2009

(30) Foreign Application Priority Data

Sep. 29, 2006 (JP) ................................. 2006-269270

(51) Int. Cl.
*G01N 5/02* (2006.01)
*G01G 3/16* (2006.01)
(52) U.S. Cl. ............................................. 73/579; 73/73
(58) Field of Classification Search ................... 73/579, 73/73, 861.18; 310/323.21
See application file for complete search history.

(56) References Cited

U.S. PATENT DOCUMENTS

| 4,616,194 A * | 10/1986 | Renoult et al. ............ 331/116 R |
| 6,397,656 B1 * | 6/2002 | Yamaguchi et al. ........... 73/1.82 |
| 7,468,608 B2 * | 12/2008 | Feucht et al. ................. 324/633 |
| 7,555,952 B2 * | 7/2009 | Onishi et al. ..................... 73/579 |
| 7,690,256 B2 * | 4/2010 | Ishii et al. ......................... 73/579 |
| 7,982,451 B2 * | 7/2011 | Onishi et al. .................. 324/71.1 |
| 2010/0021346 A1 * | 1/2010 | Wakamatsu et al. ............ 422/69 |

FOREIGN PATENT DOCUMENTS

| JP | 7-103873 | 4/1995 |
| JP | 2001-83154 | 3/2001 |
| JP | 2002-9862 | 1/2002 |
| JP | 2005-9862 | 1/2005 |

* cited by examiner

Primary Examiner — J M Saint Surin
(74) Attorney, Agent, or Firm — Jordan and Hamburg LLP (57) ABSTRACT

In a sensing instrument using a quartz sensor on whose front surface an adsorption layer for adsorbing a substance to be sensed is formed and which changes in natural frequency by the adsorption of the substance to be sensed, the present invention has an object to quickly detect a trouble of the quartz sensor to prevent an operator from recognizing an incorrect measurement result. In the present invention, a level detecting circuit detecting a signal level of an oscillation output of an oscillator circuit is provided, and after the time for stabilization passes after the power-on time, a computer takes a level detection value therein to compare the signal level and a threshold value. Then, when the signal level is lower than the threshold value, the signal level is determined as abnormal and, for example, the abnormality notification is displayed on a display unit, whereby an operator is notified of the occurrence of the abnormality.

3 Claims, 8 Drawing Sheets

SENSING INSTRUMENT

TECHNICAL FIELD

The present invention relates to a sensing instrument which uses a sensing sensor including a piezoelectric resonator changing in natural frequency by the adsorption of a sample and which senses the adsorption of the sample based on the change in the natural frequency of the piezoelectric resonator.

BACKGROUND ART

As a method for sensing a trace substance, a sensing instrument using a quartz resonator has been known. This sensing instrument has a quartz sensor in which an adsorption layer for adsorbing a substance to be sensed is formed on a front surface of the quartz resonator, and measures the presence/absence or concentration of the substance to be sensed by utilizing the fact that when the substance to be sensed is adsorbed by the quartz resonator, more particularly, the adsorption layer, its natural frequency changes according to an adsorption amount of the substance to be sensed, and this sensing instrument is advantageous in that it is applicable to a wide range and has a simple structure as an instrument, and moreover, is capable of measuring even an extremely minute amount of substance because of its high sensitivity. For example, a patent document 1 describes that the use of a quartz sensor in the analysis of a disease marker substance contained in blood, urine, and the like is an effective method alternative to an immuno-latex kit which requires an expensive, large autoanalyzer.

The present inventor has been studying the possibility of applying a quartz sensor to, for example, dioxin and PCB which are environmental pollutants, a disease marker in blood, or the like, and this method, if achieving high-precision measurement of a target substance, would be innovative. The reason is because a method using a gas-chromatography mass spectrometer and an ELISA method (enzyme-linked immunosorbent assay method), which are currently known as methods of measuring, for example, dioxin, have the following problems. The former requires an extremely high instrument cost and thus a considerably high analysis cost and takes a long period of time for analysis, and the latter is low in analysis precision, though requiring less instrument cost and analysis cost and taking a shorter period of time for analysis compared with the gas-chromatography mass spectrometer.

A major part of a sensing instrument using a quartz resonator is structured such that an adsorption layer for adsorbing a substance to be sensed, which has, for example, an antibody causing an antibody-antigen reaction, is formed on the quartz resonator, an oscillator circuit is connected to the quartz resonator, and a frequency measuring unit measuring an oscillation frequency of the oscillator circuit is provided When a CI value (crystal impedance value) of the quartz resonator is close to a negative resistance value of the oscillator circuit, signal level (amplitude) of an oscillation output becomes unstable. Further, due to some trouble, the signal level of the oscillation output sometimes becomes considerably lower than a design value. Further, the signal level sometimes becomes lower than the design value also when viscosity of a sample solution in contact with the quartz sensor is higher than a usage range. If such things happen, a correspondence relation between the concentration of a substance to be sensed in a sample solution or the like and a variation in frequency does not hold, leading to a failure in high-precision measurement of the concentration of the substance to be sensed.

However, once the measurement result is displayed, an operator recognizes the measurement result as correct, which might cause some problem. For example, if the determination result is "equal to lower than tolerable concentration" even though a toxic substance whose concentration is over a tolerable range is contained in a river, or if the determination result is "present" even though a cancer marker is not present in blood, the incorrect recognition causes a crucial situation. Since the quartz sensor is capable of measuring a substance to be sensed with extremely high precision, erroneous signal processing greatly affects subsequent operations, and therefore, if some circumstance not allowing the correct signal processing occurs, it is important to make the operator recognize this.

Patent Document 1

Japanese Patent Application Laid-open No. 2001-83154: paragraphs 0002, 0004

DISCLOSURE OF THE INVENTION

The present invention was made under such circumstances, and has an object to provide a sensing instrument using a piezoelectric resonator such as a quartz resonator whose natural frequency changes by the adsorption of a sample, the sensing instrument capable of avoiding a situation where an operator trusts the measurement result when correct signal processing cannot be performed.

The present invention is a sensing instrument which uses a sensing sensor including a piezoelectric resonator changing in natural frequency by the adsorption of a sample and which senses the adsorption of the sample based on the change in the natural frequency of the piezoelectric resonator, the instrument including:

an oscillator circuit oscillating the piezoelectric resonator;

a measuring unit measuring a signal regarding a frequency of an oscillation output of the oscillator circuit;

a level detecting circuit detecting a signal level of the oscillation output of the oscillator circuit;

a level determinator determining that the signal level is normal when the signal level detected by the level detecting circuit is equal to or higher than a threshold value, and determining that the signal level is abnormal when the signal level is lower than the threshold value; and a notifier notifying that the signal level is abnormal when the signal level is determined as abnormal by the level determinator.

As the piezoelectric resonator, usable is, for example, one which includes: an electrode provided on a front surface of a piezoelectric piece; and an adsorption layer formed on a front surface of the electrode to adsorb a substance to be sensed, and changes in the natural frequency when the substance to be sensed is adsorbed.

A timing at which the level determinator makes the determination on the signal level is, for example, after a preset time for stabilization passes after power is supplied to the sensing instrument.

According to the present invention, in the sensing instrument using the piezoelectric resonator, for example, the quartz resonator whose natural frequency changes by the adsorption of the sample, the signal level (amplitude) of the oscillation output of the oscillator circuit is detected and it is notified that the signal level is abnormal when the signal level is lower than the threshold value, which makes it possible to quickly detect a trouble of a quartz sensor or the like to prevent the measurement result from being recognized as correct when there is a trouble in the quartz sensor or the like.

BEST MODE FOR CARRYING OUT THE INVENTION

Figure 1:
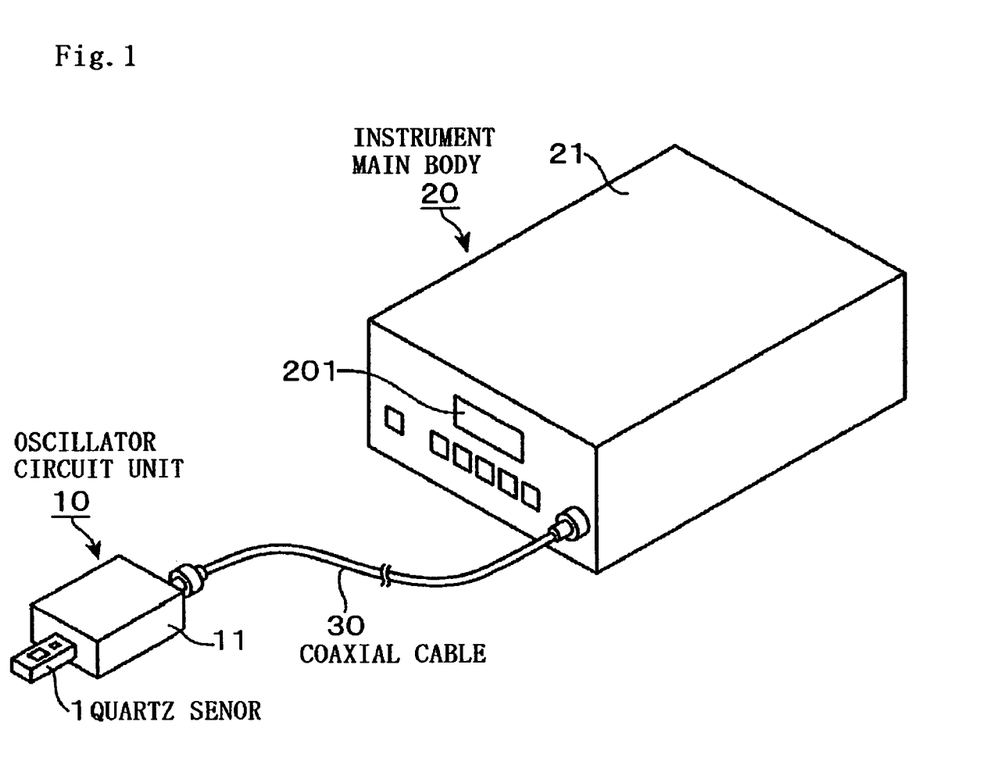
FIG. 1 is a perspective view showing an outer appearance of an embodiment of a sensing instrument according to the present invention.
Figure 3:
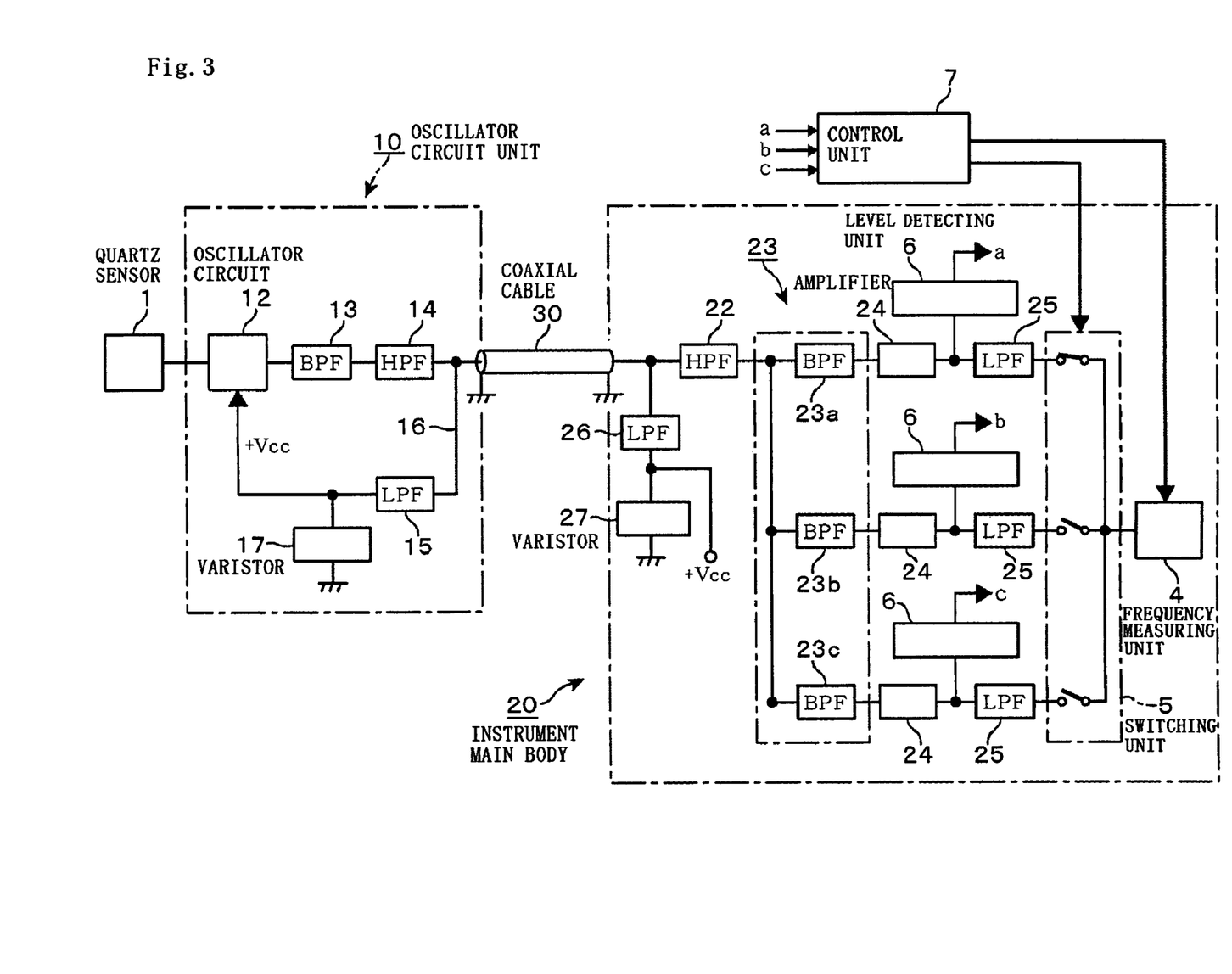
FIG. 3 is a block circuit diagram showing the whole circuit configuration of the embodiment.

Hereinafter, an embodiment of a sensing instrument according to the present invention will be described. As shown in FIG. 1 and FIG. 3, the sensing instrument includes an oscillator circuit unit 10 and an instrument main body 20, and the oscillator circuit unit 10 can be attachably/detachably connected to the instrument main body 20 by a cable, for example, a coaxial cable 30.

The oscillator circuit unit 10 has in its casing 11 an oscillator circuit 12, a band-pass filter (band filter) 13 which allows the passage of a signal with a resonance frequency of the oscillator circuit 12 (a main oscillation frequency of a later-described quarts resonator), and a high-pass filter 14.

Figure 2:
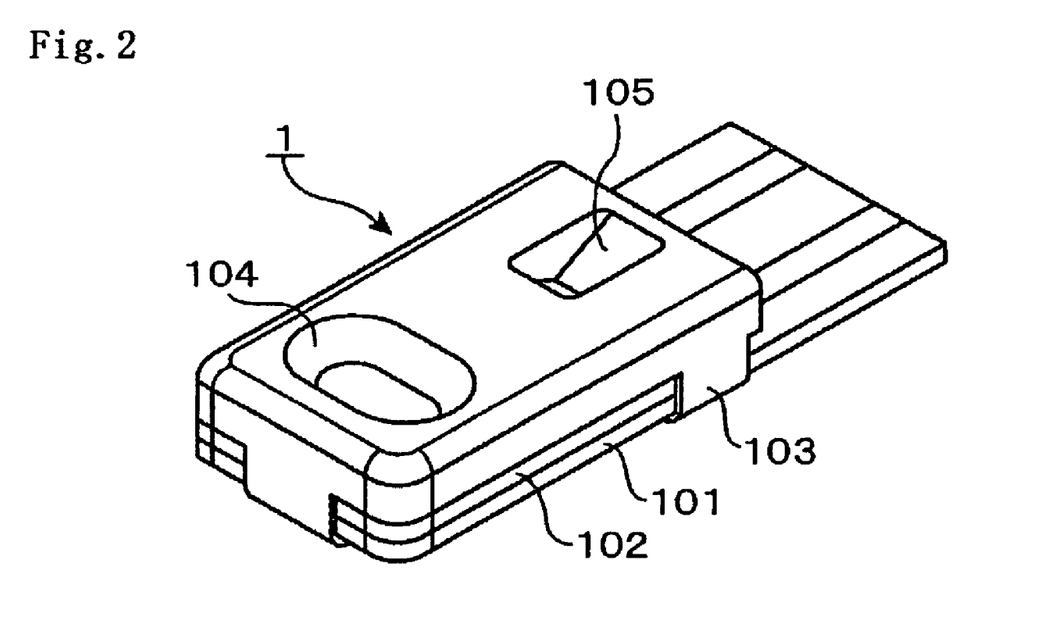
FIG. 2 is a perspective view of a quartz sensor used in the embodiment.

Further, a quartz sensor 1 which is a sensing sensor is attachably/detachably connected to the oscillator circuit unit 10. Since the quartz sensor 1 is generally known, only an example of its outer appearance is shown in FIG. 2, and the quartz sensor 1 is structured such that a rubber sheet 102 is stacked on a printed circuit board 101 as a wiring board whose one end is a connection terminal, a quartz resonator as a piezoelectric resonator is disposed to cover a recessed portion provided in the rubber sheet 22, and an upper cover case 103 is mounted from an upper side of the rubber sheet 102. In the upper cover case 103, an injection port 104 for sample solution and a check port 105 for sample solution are formed, and the sample solution is injected from the injection port 104 to fill an upper surface-side space of the quartz resonator. The recessed portion on a lower surface side of the quartz resonator is an airtight space, whereby the quartz sensor of a Languban type is formed.

In the quartz resonator, excitation electrodes are formed on both surfaces of its quartz piece, and an adsorption layer for adsorbing a substance to be sensed is formed on a front surface of the excitation electrode. In a case where the substance to be sensed is, for example, an antigen such as protein, an antibody for capturing the antigen by an antigen-antibody reaction is used as the adsorption layer.

A circuit of the instrument main body 20 is housed in the casing 21 on whose front surface a display unit 201 and so on are provided, the display unit 201 displaying the result of measurement, for example, a frequency, a variation in the frequency, or the like by, for example, lighting LED. In the circuit, a high-pass filter 22 and a frequency sorting circuit 23 in which a plurality of, for example, three band-pass filters (band filters) 23a to 23c for sorting frequencies are connected in parallel are provided along a signal line of a frequency signal from the oscillator circuit 12, and a series circuit of an amplifier 24 and a low-pass filter 25 is connected to each of output sides of the band-pass filters 23a to 23c. Three signal lines branching off at the frequency sorting circuit 23 from the signal line are called channels, and there is further provided a switching unit 5 selectively connecting downstream ends of the channels (output ends of the low-pass filters 25) to a frequency measuring unit 4 as a measuring unit.

The band-pass filters 23a to 23c are intended to selectively allow the passage of signals with frequencies corresponding to oscillation frequencies of the used oscillator circuit units 10, and if, for example, three 9 MHz, 30 MHz, and 60 MHz oscillator circuits are selected for use as the oscillator circuit units 10, band-pass filters corresponding to these frequencies are prepared.

Here, a power source of the instrument main body 20 and the oscillator circuit unit 10 will be described. A direct-current voltage +Vcc supplied to the circuit in the oscillator circuit unit 10 is connected to the signal line on an input side of the high-pass filter 22 via a low-pass filter 26. In the oscillator circuit unit 10, a power supply line 16 in which a low-pass filter 15 is inserted branches off from the signal line on an output side of a high-pass filter 14. 17, 27 denote varistors. With such a structure, the direct-current voltage on the instrument main body 20 side is superimposed on the signal line to be sent via a core wire of the coaxial cable 30 into the oscillator circuit unit 10, and the direct-current voltage +Vcc is not sent to the oscillator circuit 12 side via the high-pass filter 14 but is obtained through the low-pass filter 15. Therefore, in the oscillator circuit unit 10, the direct-current voltage +Vcc can be supplied to the oscillator circuit 12 and so on, and thus a direct-current power source need not be mounted, leading to a simple structure. An outer conductor of the coaxial cable 30 is grounded in the oscillator circuit unit 10 and the instrument main body 20.

Figure 4:
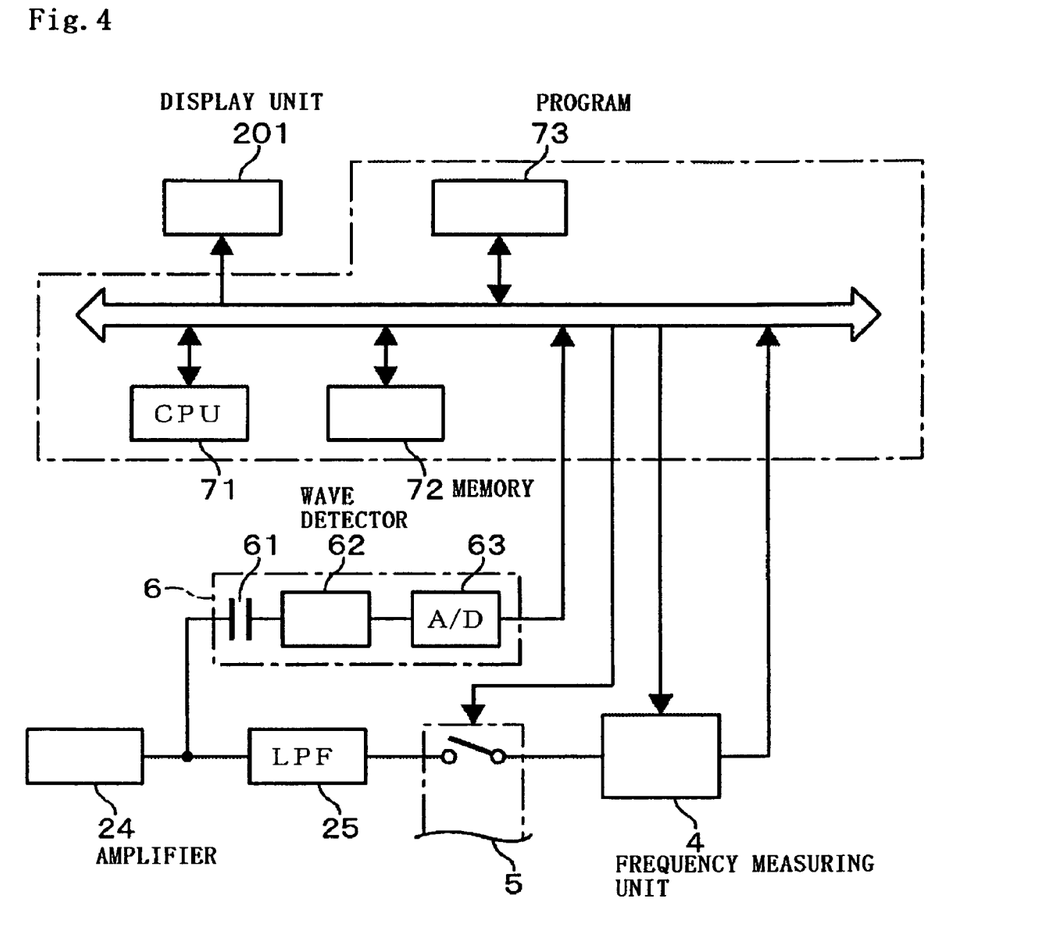
FIG. 4 is a block diagram showing a level detecting circuit and a control unit.

Further, in the instrument main body 20, level detecting units 6 are provided to detect signal levels (amplitudes) at output sides of the amplifiers 24 of the aforesaid channels respectively. As shown in FIG. 4, the level detecting units 6 each include a capacitor 61 for cutting a direct current of the amplifier 24, a wave detector 62, and an analog/digital (A/D) converter 63, and the signal levels detected here are input to a control unit 7 formed by a computer.

The control unit 7 includes a CPU 71, a work memory 72, and a program 73 for executing a series of processing necessary for the frequency measurement. Actually, the program 73 is stored in a ROM but is illustrated in a simplified manner. The program includes steps of sequentially connecting the three channels to the frequency measuring unit 4, comparing a level detection value of the connected channel with a threshold value, controlling the switching unit 5 so that the switching unit 5 connects this channel to the frequency measuring unit 4 if the level detection value is equal to or higher than the threshold value, and outputting a control signal so as to enable the measurement appropriate for the frequency corresponding to the channel. As will be described later, the program 73 further includes the steps of determining, based on the level detection value, whether or not the operation of the instrument, for example, an oscillation operation of the quartz sensor 1 has a trouble and displaying an abnormal state.

At the time of the detection of the signal level of each of the channels, the channel is preferably connected to the frequency measuring unit 4. The reason is that if the signal level is detected while the output end of the channel is left open, a value of a terminal impedance at the time of the detection and a value of a terminal impedance at the time of the measurement of the frequency by the frequency measuring unit 4 become different, which lowers accuracy of the detection of the signal level.

In this example, the frequency measuring unit 4 calculates a variation in frequency by digital processing based on a frequency signal corresponding to a difference between a frequency of the frequency signal from the oscillator circuit unit 10 and a frequency of a reference frequency signal, as will be described later, and different reference frequency signals need to be used depending on the oscillation frequencies of the used oscillator circuit units 10. Therefore, in this program, by finding a channel having the level detection value equal to or higher than the threshold value, it is possible to specify to which of bands of the band-pass filters 23a to 23c the frequency of the frequency signal corresponds. That is, the oscillation frequency of the oscillator circuit unit 10 connected to the instrument main body 20 is known. Therefore, the control signal for selecting the reference frequency corresponding to this frequency, for example, the control signal validating one of three reference frequency output units is output.

Next, the operation of the above-described embodiment will be described. First, upon power on of the instrument main body 20 side, the direct-current voltage is supplied to the internal circuit of the instrument main body 20 and at the same time, the direct-current voltage is supplied to the oscillator circuit unit 10 side via the coaxial cable 30 as previously described. It is assumed here that the oscillator circuit units 10 of three kinds, that is, one with 9 MHz, one with 30 MHz, and one with 60 MHz are usable, and the 9 MHz oscillator circuit unit 10 is currently connected to the instrument main body 20, and the 9 MHz quartz sensor 1 is inserted in this oscillator circuit unit 10. Then, in order to calculate a blank value, for instance, a solution not containing a substance to be sensed is injected into the quartz sensor 1, and the quartz resonator 24 is oscillated. This solution may be pure water or other solution.

Figure 5:
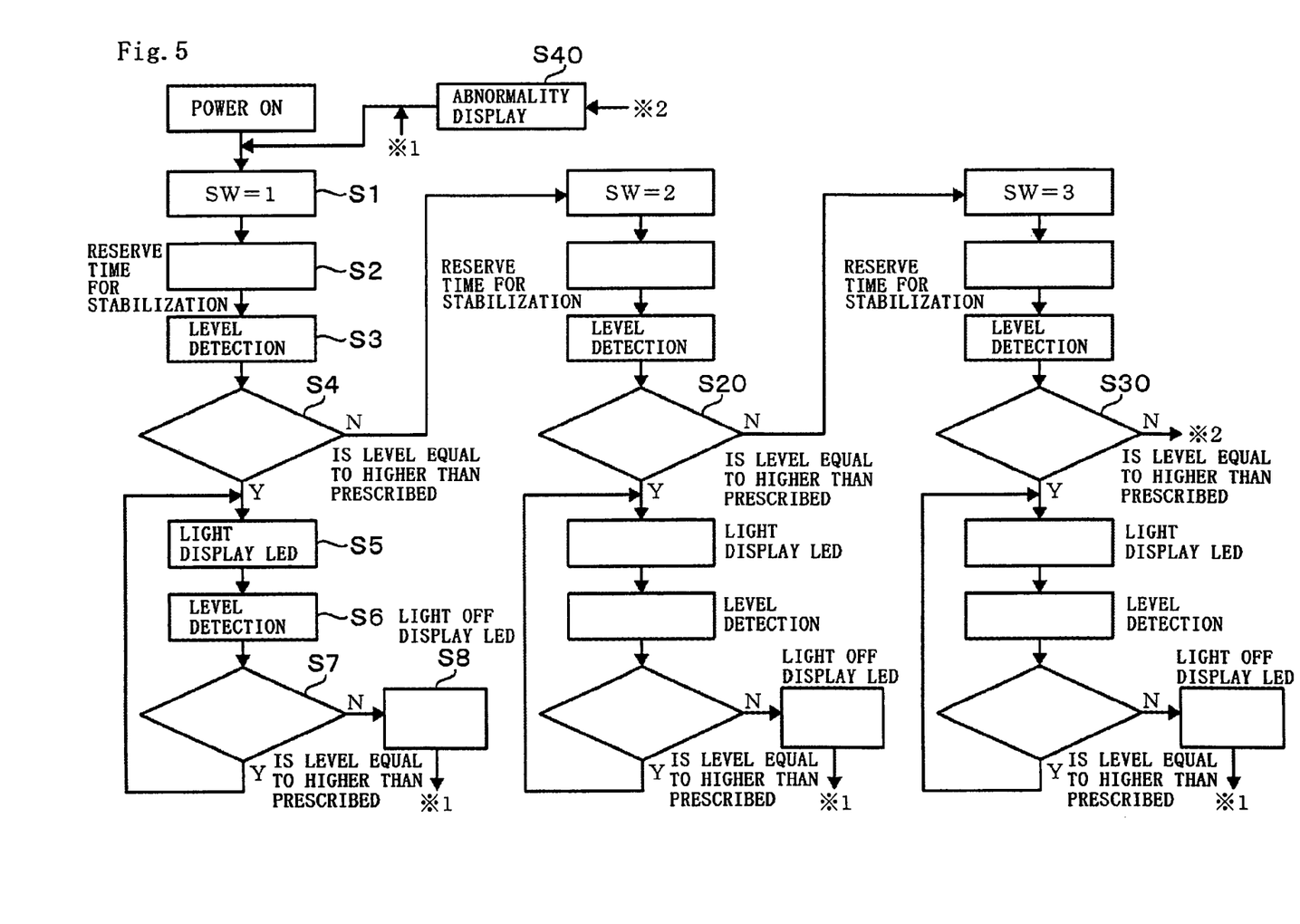
FIG. 5 is a flowchart showing part of the operation of the embodiment.

At this time, in the program 73, the steps proceed as shown in FIG. 5. Here, for convenience of description, the channel in which the 9 MHz band-pass filter 23a is provided is defined as a channel 1, the channel in which the 30 MHz band-pass filter 23b is provided is defined as a channel 2, and the channel in which the 60 MHz band-pass filter 23c is provided is defined as a channel 3. First, the switching unit 3 selects the channel 1 to connect the channel 1 to the frequency measuring unit 4 (Step S1), and after the time required for the operation of the oscillator circuit 12 to stabilize and for the frequency signal to be stabilized, for example, one second passes after the power-on time (Step S2), the signal level of the channel 1 is detected and it is determined whether or not the signal level is equal to or higher than the threshold value (Steps S3 and S4). When the signal level is equal to or higher than the threshold value, the LED of the display unit 201 is lighted (Step S5). That is, in this case, it is known that the oscillation frequency of the oscillator circuit unit 10 is 9 MHz since the pass band of the band-pass filter 23a of the channel 1 is 9 MHz, and therefore, a 10 MHz reference frequency which is a reference frequency used for the 9 MHz measurement in the frequency measuring unit 4 is selected for the frequency measurement. An example of this measurement will not be described in detail here in order to avoid the complication of the description.

After the completion of such frequency measurement, the result of the measurement, in this example, a difference frequency between the frequency of the frequency signal from the oscillator circuit unit 10 and the reference frequency is displayed on the display unit 201, and the lighted LED enables an operator to confirm the result. In the flow in FIG. 5, no description is given regarding the measurement, and therefore, after the display LED is lighted, the detection of the signal level of the channel 1 and the determination regarding the signal level are performed again (Steps S6, S7), and when the level is equal to or higher than the threshold value, Steps S5 to S7 are repeated. When the quartz sensor 1 is detached after the end of the measurement, the control leaves Step 7 and returns to Step S1 after the display unit 201 is lighted off (Step S8).

On the other hand, when the signal level of the channel 1 is lower than the threshold value, the switching unit 3 switches the channel 1 to the channel 2, and the same steps are performed. Specifically, when it is determined at Step 20 that the signal level of the channel 2 is equal to or higher than the threshold value, it is known that the oscillation frequency of the oscillator circuit unit 10 is 30 MHz, and a 31 MHz reference frequency which is a reference frequency used for the 30 MHz measurement in the frequency measuring unit 4 is selected for the frequency measurement, and the result of the measurement is displayed on the display unit 201 in the same manner.

Further, when it is determined at Step 20 that the signal level of the channel 2 is lower than the threshold value, the switching unit 3 switches the channel 2 to the channel 3, and the same steps are performed. Then, when it is determined at Step S30 that the signal level of the channel 2 is lower than the threshold value, this means that the levels of all of the 9 MHz, 30 MHz, 60 MHz frequency signals are lower than the threshold value, in other words, this implies that the quartz sensor 1 has some trouble. Therefore, at Step S40, abnormality notification is displayed on the display unit 201, and thereafter, the control returns to Step S1. In the program 73, the steps cyclically proceed, but as the operation of the instrument, the abnormality notification is kept displayed on the display unit 201. An example of a method of this abnormality display is to display, for example, "signal level is low".

It is not necessary to perform Step S40 for the abnormality display, and in this case, an operator can recognize that the abnormality is occurring since the display unit 201 is kept lighted off. Alternative methods of notifying a trouble may be a method of lighting an abnormality lamp, a method of sounding an abnormality buzzer, and the like.

Furthermore, after it is determined for one channel that the signal level is equal to or higher than the threshold value, the step of confirming for another channel that the signal level is lower than the threshold value may be added to the flow shown in FIG. 5, and the abnormality notification may be displayed when the signal levels of two channels or more are equal to or higher than the threshold value. In this case, it can be inferred, for example, that the quartz sensor 1 is oscillating with an intermediate frequency between the frequencies assigned to two kinds of the oscillator circuit units 10 (for example, a frequency between 9 MHz and 30 MHz), and the correct measurement is not possible in this case.

Returning to the description of the case where the oscillation of the quartz sensor 1 is normal, after the frequency measurement is performed when a set amount of the solution not containing the substance to be sensed is put into the quartz sensor 1 as described above, a sample solution which is to undergo the measurement of a substance to be sensed is injected into the quartz sensor 1 containing the aforesaid solution, and the oscillation frequency of the quartz resonator of the quartz sensor 1 after the sample solution is put therein is found. For example, if the 9 MHz quartz sensor 1 is used, the frequency measurement proceeds while Steps S5 to S7 in FIG. 5 are repeated, and the frequency is displayed on the display unit 201. Then, a variation in the frequency after the sample solution is put is found, and the concentration of the substance to be sensed in the quartz sensor 1 is known by, for example, the use of a calibration curve, and as a result, the concentration of the substance to be sensed in the sample solution is known.

According to the above-described embodiment, in the sensing instrument using the quartz sensor 1, the signal level (amplitude) of the oscillation output of the oscillator circuit 12 is detected, and though the main purpose of this level detection is to specify the frequency of the frequency signal from the oscillator circuit unit 10, the abnormality of the instrument can be detected by this level detection. Specifically, it is determined whether or not the levels of all the channels are lower than the threshold value, and when the levels of all the channels are lower than the threshold value, it means that the signal level of the frequency signal sent from the oscillator circuit unit 10 is lower than the threshold value. Therefore, in this case, the abnormality is notified, which makes it possible to quickly detect a trouble of a quartz sensor or the like, prevent the measurement result from being recognized as correct when a trouble is occurring in the quartz sensor or the like, and avoid a later problem ascribable to the erroneous measurement result.

Further, the above-described embodiment has the following advantages. In adopting the structure in which the oscillator circuit unit 10 and the instrument main body 20 are formed separately, a plurality of, three in this example, band-pass filters 23a to 23c having the pass characteristics corresponding to the oscillation frequencies of the oscillator circuits 12 are provided in the instrument main body 20 side to sort the frequency signals, and the levels of the sorted frequency signals are detected. Therefore, it is possible to specify which of the channels (the band-pass filters 23a to 23c) has the signal level equal to or higher than the threshold value, based on the detection value of the signal level, and as a result, it is possible to know the oscillation frequency of the oscillator circuit unit 10. As a result, it is possible to control the switching unit so as to connect this channel to the measuring unit and to set the reference frequency used in the frequency measuring unit 4 to a value according to the oscillation output, which enables the frequency measurement. Therefore, it is possible to separately form the oscillator circuit unit 10 and the instrument main body 20 and select the oscillator circuit unit 10 with a proper frequency for the substance to be sensed, out of the plural kinds of frequencies, and in addition, to make the instrument main body 20 common to the oscillator circuit units 10.

In the present invention, the structure of the instrument is not limited to the structure in which three kinds of the oscillator circuit units 10 are usable as described above, but may be a structure in which one kind of the oscillator circuit unit 10, or one selected from two kinds or four kinds or more of the oscillator circuit units 10 can be connected to the instrument main body 20. Further, the measurement by the frequency measuring unit 4 is not limited to the direct measurement of the frequency, but the frequency measuring unit 4 may detect a phase of the frequency signal and as a result detect the frequency.

In an instrument using only one kind of the oscillator circuit unit 10, one channel is provided instead of the three channels shown in FIG. 3. That is, on the subsequent stage of the high-pass filter 22, there is only one signal line instead of the three branching signal lines, and this signal line is connected to the frequency measuring unit 4. In this case, the switching unit 5 is not required.

Figure 6:
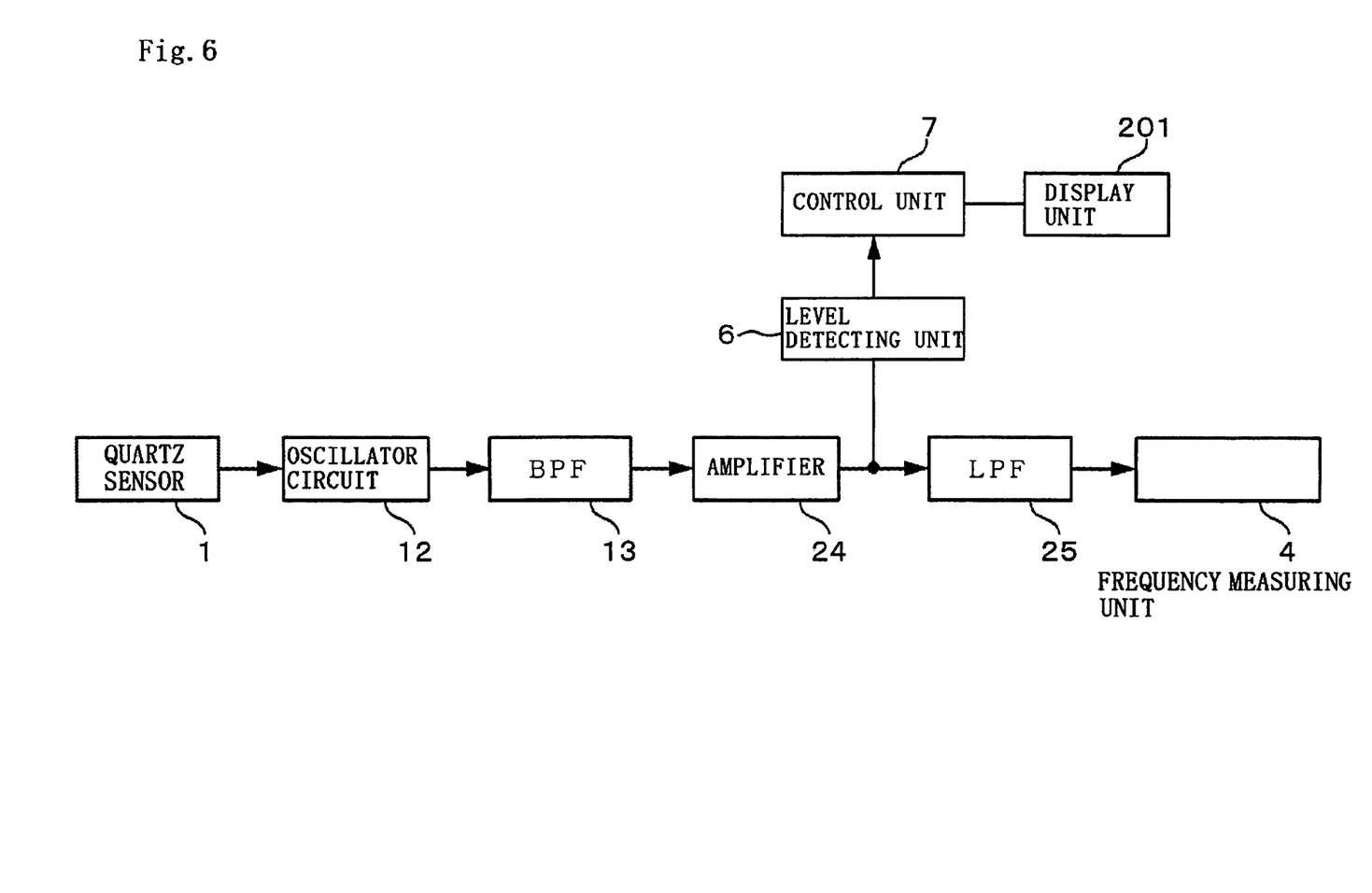
FIG. 6 is a block circuit diagram showing the whole circuit configuration of another embodiment of the present invention.

The present invention is applicable not only to the instrument in which the instrument main body 20 and the oscillator circuit unit 10 are formed separately and the instrument adaptable to a plurality of frequencies as described above, but also to an instrument shown in FIG. 6, for instance. In the instrument in FIG. 6, one kind of frequency is used for a quartz sensor 1, a signal level at an output side of an amplifier 24 is detected by a level detecting unit 6, and after the time for frequency stabilization passes from the power-on time, the control unit 7 determines whether or not the level detection value is equal to or higher than a threshold value, and performs abnormality display when the level detection value is lower than the threshold value. Note that in FIG. 6, parts denoted by the same reference numerals as those in FIG. 3 are parts which are the same as or corresponding to the parts in FIG. 3.

Figure 7:
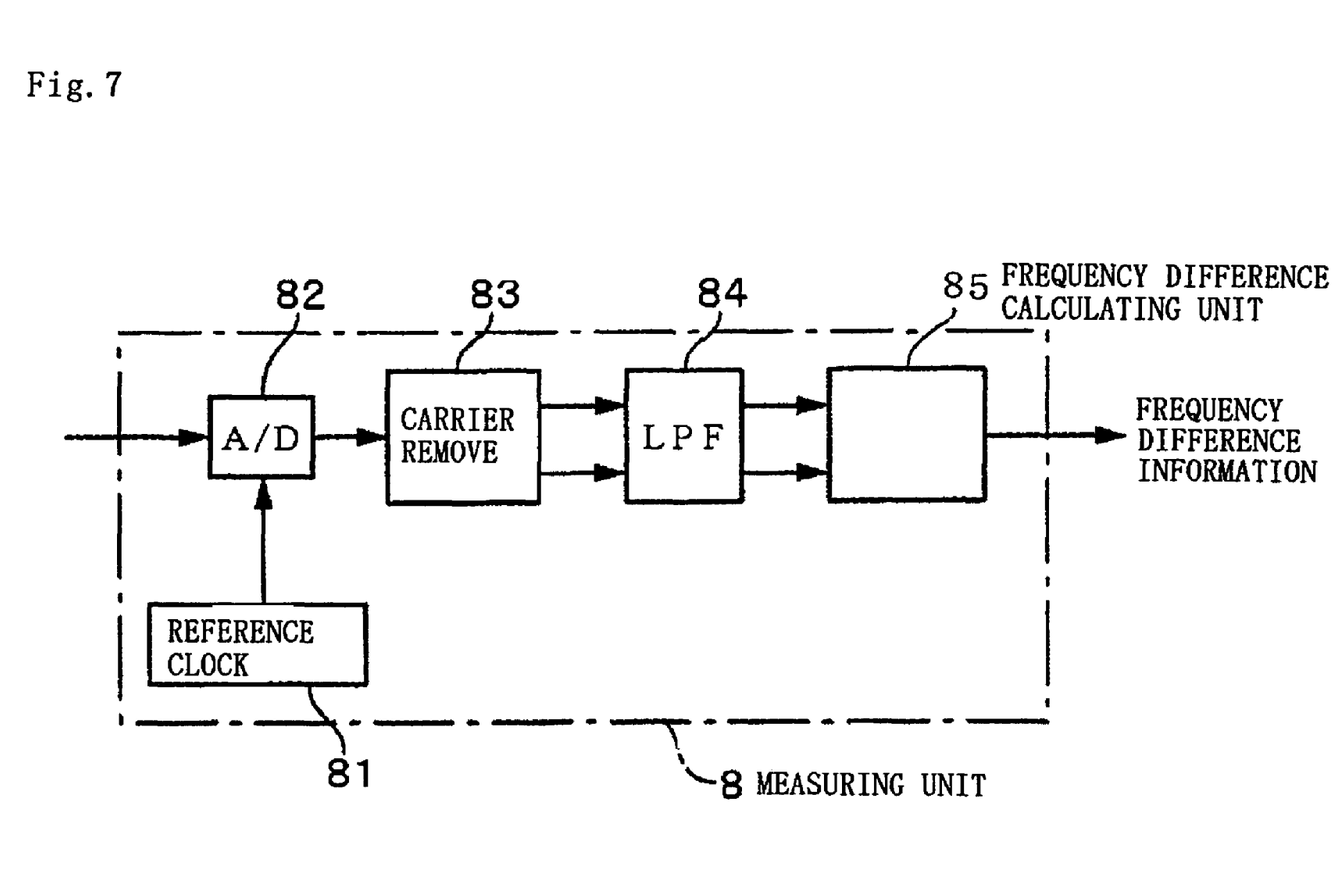
FIG. 7 is a block diagram showing an example of a measuring unit.

Here, an example of the frequency measuring unit 4 is shown in FIG. 7. In FIG. 7, 81 denotes a reference clock generating unit, and it outputs a clock signal, which is a frequency signal with extremely stable frequency, in order to sample the frequency signal from the switching unit 5. 82 denotes an A/D (analog/digital) converter, and it samples the frequency signal based on the clock signal from the reference clock generating unit 81 and outputs the sampling value as a digital signal. For example, when fc is 9 MHz, fs is set to 10 MHz, where fc is the frequency of the frequency signal and fs is the sampling frequency (frequency of the clock signal). In this case, a fundamental wave of the frequency signal specified by the output signal from the A/D converter 61 which is the digital signal is a 1 MHz sinusoidal wave. To be more specific, 9 MHz and 1 MHz mentioned here is 9.2 MHz and 0.8 MHz, but they are written as rough values for convenience sake.

On a subsequent stage of the A/D converter 82, a carrier remove 83 and a low-pass filter 84 are provided in this order. The carrier remove 83 and the low-pass filter 84 are used to extract a rotation vector which rotates at a frequency corresponding to a difference between, for example, the frequency of the 1 MHz sinusoidal signal specified by the digital signal from the A/D converter 82 and the frequency of a sinusoidal signal used for quadrature detection.

Figure 8:
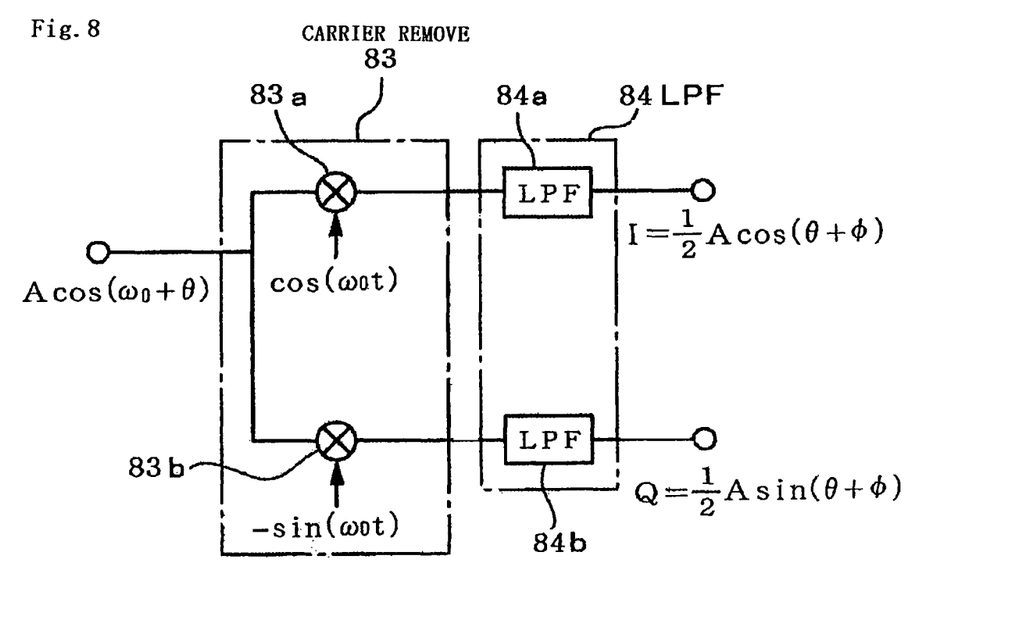
FIG. 8 is a block diagram showing part of the circuit block shown in FIG. 7.

For easier understanding of the operation of extracting the rotation vector, the sinusoidal signal specified by the digital signal from the A/D converter 82 is defined as $A\cos(\omega 0t+\theta)$. As shown in FIG. 8, the carrier remove 83 includes a multiplying unit 83a multiplying the sinusoidal signal by $\cos(\omega 0t)$ and a multiplying unit 83b multiplying the sinusoidal signal by $-\sin(\omega 0t)$. That is, by such arithmetic operation, the quadrature detection is performed. An output of the multiplying unit 83a and an output of the multiplying unit 83b are expressed by an expression (2) and an expression (3) respectively.

$$A\cos(\omega 0t+\theta)\cdot\cos(\omega 0t) = \tfrac{1}{2}\cdot A\cos\theta + \tfrac{1}{2}\{\cos(2\omega 0t)\cdot\cos\theta + \sin(2\omega 0t)\cdot\sin\theta\} \quad (2)$$

$$A\cos(\omega 0t+\theta)\cdot-\sin(\omega 0t) = \tfrac{1}{2}\cdot A\sin\theta - \tfrac{1}{2}\{\sin(2\omega 0t)\cdot\cos\theta + \cos(2\omega 0t)\cdot\sin\theta\} \quad (3)$$

Therefore, when the output of the multiplying unit 83a and the output of the multiplying unit 83b are passed through low-pass filters 84a and 84b respectively, the $2\omega 0t$ frequency signal is filtered out, and as a result, $\tfrac{1}{2}\cdot A\cos\theta$ and $\tfrac{1}{2}\cdot A\sin\theta$ are extracted from the low-pass filter 84.

Then, when the frequency of the sinusoidal signal expressed as $A\cos(\omega 0t+\theta)$ changes, $A\cos(\omega 0t+\theta)$ becomes $A\cos(\omega 0t+\theta+\omega 1t)$. Note that $\omega 1$ is sufficiently smaller than $\omega 0$. Therefore, $\frac{1}{2}\cdot A\cos\theta$ becomes $\frac{1}{2}\cdot A\cos(\theta+\omega 1t)$, and $\frac{1}{2}\cdot A\sin\theta$ becomes $\frac{1}{2}\cdot A\sin(\theta+\omega 1t)$. That is, the output obtained from the low-pass filter 84 is a signal corresponding to a variation $\omega 1/2\pi$ of the frequency of the sinusoidal signal [$A\cos(\omega 0t+\theta)$]. That is, these values are a real part (I) and an imaginary part (Q) which are complex expression of the rotation vector rotating at the frequency corresponding to the difference between the frequency of the sinusoidal signal specified by the digital signal from the A/D converter 82 and the frequency $\omega 0/2\pi$ of the sinusoidal signal used for the quadrature detection.

Figure 9:
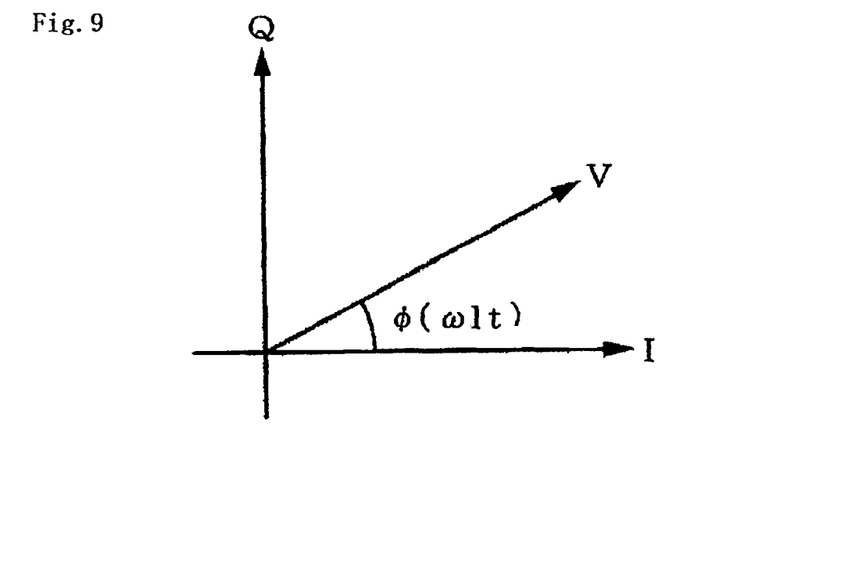
FIG. 9 is an explanatory chart showing a rotation vector extracted by the block diagram shown in FIG. 9.

FIG. 9 is a chart showing this rotation vector and an angular velocity of this rotation vector is $\omega 1$. Therefore, if there is no change in the frequency of the sinusoidal signal, $\omega 1t$ is zero and thus the rotation speed of the rotation vector is zero, but when due to the adsorption of the substance to be sensed by the quartz resonator 24, the frequency of the quartz resonator changes and accordingly the frequency of the sinusoidal signal changes, the rotation vector rotates at the rotation speed corresponding to the variation.

Incidentally, the angular velocity corresponding to the oscillation frequency of the quartz resonator in the absence of a substance to be sensed rarely agrees with the angular velocity of the sinusoidal signal used for the quadrature detection, and therefore, in actual practice, the angular velocity of the rotation vector corresponding to the oscillation frequency of the quartz resonator in the absence of the substance to be sensed and the angular velocity of the rotation vector corresponding to the oscillation frequency of the quartz resonator in the presence of the substance to be sensed are found, and a difference between the angular velocities is found. The difference between the angular velocities of the rotation vector is a value corresponding to the variation in the frequency of the quartz resonator caused by the adsorption of the substance to be sensed by the quartz resonator.

The invention claimed is:

1. A sensing instrument which uses a sensing sensor including a piezoelectric resonator changing in natural frequency by the adsorption of a sample and which senses the adsorption of the sample based on the change in the natural frequency of the piezoelectric resonator, the instrument comprising:
   an oscillator circuit oscillating the piezoelectric resonator;
   a measuring unit measuring a signal regarding a frequency of an oscillation output of the oscillator circuit;
   a level detecting circuit detecting a signal level of the oscillation output of the oscillator circuit;
   a level determinator determining that the signal level is normal when the signal level detected by the level detecting circuit is equal to or higher than a threshold value, and determining that the signal level is abnormal when the signal level is lower than the threshold value; and
   a notifier notifying that the signal level is abnormal when the signal level is determined as abnormal by the level determinator.

2. The sensing instrument according to claim 1, wherein the piezoelectric resonator includes: an electrode provided on a front surface of a piezoelectric piece; and an adsorption layer formed on a front surface of the electrode to adsorb a substance to be sensed, and changes in the natural frequency when the substance to be sensed is adsorbed.

3. The sensing instrument according to claim 1, wherein a timing at which the level determinator makes the determination on the signal level is after a preset time for stabilization passes after power is supplied to the sensing instrument.

* * * * *